(12) United States Patent
Sakuma et al.

(10) Patent No.: US 6,623,431 B1
(45) Date of Patent: Sep. 23, 2003

(54) EXAMINATION METHOD OF VASCULAR ENDOTHELIUM FUNCTION

(75) Inventors: Ichiro Sakuma, 719-24, Kawashima-cho, Hodogaya-ku, Yokohama-shi, Kanagawa-ken (JP); Takeyoshi Dohi, Tokyo (JP); Yasuyoshi Ouchi, Tokyo (JP); Masao Yoshizumi, Tokyo (JP)

(73) Assignee: Ichiro Sakuma, Yokohama (JP)

( * ) Notice: Subject to any disclaimer, the term of this patent is extended or adjusted under 35 U.S.C. 154(b) by 0 days.

(21) Appl. No.: 10/224,666

(22) Filed: Aug. 21, 2002

(30) Foreign Application Priority Data

Feb. 25, 2002 (JP) ........................................ 2002-048057

(51) Int. Cl.⁷ .............................. A61B 8/00; A61B 5/00
(52) U.S. Cl. ......................... 600/443; 600/417; 600/449
(58) Field of Search ................................ 600/407–471, 600/300, 481, 486, 508; 73/620–633; 367/7, 11, 130, 138; 128/898, 916; 348/65; 606/2, 13–17, 130; 601/2–4; 604/20

(56) References Cited

U.S. PATENT DOCUMENTS

| | | | | |
|---|---|---|---|---|
| 5,408,409 A | * | 4/1995 | Glassman et al. | 600/407 |
| 5,662,111 A | * | 9/1997 | Cosman | 600/407 |
| 5,749,362 A | * | 5/1998 | Funda et al. | 600/407 |
| 5,840,018 A | * | 11/1998 | Michaeli | 600/300 |
| 6,233,476 B1 | * | 5/2001 | Strommer et al. | 600/424 |

FOREIGN PATENT DOCUMENTS

| | | |
|---|---|---|
| JP | 2000-229078 | 8/2000 |
| JP | 2000-271117 | 10/2000 |
| JP | 2001-2999752 | 10/2001 |

OTHER PUBLICATIONS

"Exception to Lack of Novelty", The 17ᵗʰ Regular Meeting of the Japanese Life Support Society, Aug. 24, 2001, Japan Medical University, Filed Mar. 8, 2002, Japanese Patent Office.

* cited by examiner

Primary Examiner—Ali M. Imam
(74) Attorney, Agent, or Firm—Carella, Byrne, Bain, Gilfillan, Cecchi et al.; Elliot Olstein; William Squire

(57) ABSTRACT

A rapid vascular endothelium function examining method with improved reproducibility is provided. An apparatus for the method comprises systems for acquiring ultrasound images by an ultrasound probe, processing the acquired images and moving/rotating the ultrasound probe. The method comprises: a first step where the acquired image is processed so that the center of a blood vessel is laid on the center of the image; a second step where a series of operations for acquiring an image, processing the acquired image and moving the probe based on the processed result, are repeated so that the probe is moved in parallel to the blood vessel; a third step where the similar operations to the second step are executed so that the probe is moved in parallel to and immediately above the blood vessel; a fourth step for determining a blood vessel diameter from the finally acquired image at the third step.

9 Claims, 5 Drawing Sheets

EXAMINATION METHOD OF VASCULAR ENDOTHELIUM FUNCTION

BACKGROUND OF THE INVENTION

1. Field of the Invention

The present invention relates to a probing system of vascular endothelium functions, particularly relates to a probing method where a positioning operation with the aid of a robot arm and an image processing operation are combined.

2. Brief Description of the Related Art

Arterial scleroses, a main cause of a cerebrovascular disease infarction and a myocardial infarction among three major causes of death in the Japanese, have been increasing as diets of the Japanese have been westernized. Consequently, noninvasive and simple probing methods to detect such arterial scleroses at their early stages, have been required.

An Examination method of a vascular endothelium function is used as one of such examination methods. In this method, a function of the vascular endothelium (i.e. inner most cell layers of a vascular wall which regulate vasodilation/vasoconstriction by releasing a vasodilator) is measured. In an examination procedure of the vascular endothelium function, after a blood vessel diameter at rest is determined, a lower portion of the arm is avascularized for 5 minutes by applying 250 mmHg of pressure with a cuff around the arm and released so as to generate a vascular dilating reaction caused by blood flow. An increased rate of a blood vessel diameter due to flow mediated vasodilation against the blood vessel diameter at rest is used as an index to evaluate arterial sclerosis. Hashimoto et al. reported in a Japanese medical journal (*Rinsho-i* (1998): 24(5) pp789–791) that a dilated degree in a subject with a slight arterial sclerosis is ca. 10% while a dilated degree in a subject with a grave arterial sclerosis is lowered to ca. 2%.

They determined blood vessel diameters in such a manner that after an ultrasound probe was applied to an arm of a subject and a appropriate blood vessel image along its longitudinal direction is acquired and stored for determining blood vessel diameters. They recognized the blood vessel walls in the acquired image by their naked eyes and the blood vessel diameters are determined based on the recognized walls.

Fan et al. determined the blood vessel diameters by processing images acquired by medical doctors (*IEEE Transaction on Medical Imaging*: Vol. 19, No. 16, June 2000, pp621–631).

However, in the method by Hashimoto et al., it takes a fairly long time to acquire images and reproducibility of the determined blood vessel diameters is poor because walls are recognized by naked eyes. Further, it is reported that in the method by Fan et al. determined results largely depend on images even when images are selected from the same subject.

SUMMARY OF THE INVENTION

The present invention is carried out to solve the problems mentioned above and to provide an examination method of the vascular endothelium function by combining a positioning operation with the aid of a robot arm and an image processing operation. The present invention attains a more rapid examination method with improved reproducibility when determining blood vessel diameters.

More specifically, the present invention having the following arrangements (1) to (9) solve the problems mentioned above.

(1) A method of examining a vascular endothelium function by an automatic measurement system comprising: a measuring system comprising an ultrasound diagnostic device and an ultrasound probe attached to the ultrasound diagnostic device for acquiring an ultrasound image; an image processing and calculating system comprising a computer and an image processing board for processing the acquired ultrasound image by the measuring system; and a navigation system comprising a robot arm for moving and rotating the ultrasound probe, wherein the method comprises steps of: a first step wherein an ultrasound image is acquired after the ultrasound probe is moved to a subject portion for probing its vascular endothelium function and the acquired image is processed for calculating and controlling a position of the ultrasound probe so that the center of a blood vessel to be probed is laid on the center of the image; a second step wherein a series of operations comprising an operation for acquiring ultrasound image, an operation for processing and calculating the acquired ultrasound image and an operation for moving the robot arm based on the calculated result, are repeated starting from the finally acquired ultrasound image at the first step so that the ultrasound probe is moved to in a parallel position to the center line of the blood vessel; a third step wherein a series of operations comprising an operation for acquiring ultrasound image, an operation for processing and calculating the acquired ultrasound image and an operation for moving the robot arm based on the calculated result, are repeated starting from the finally acquired ultrasound image at the second step so that the ultrasound probe is moved to a position where the ultrasound probe is in parallel to and immediately above the center line of the blood vessel; and a fourth step wherein a blood vessel diameter is determined from the finally acquired ultrasound image at the third step.

(2) The method according to (1), wherein: the center of gravity of a color Doppler signal area in the acquired ultrasound image is recognized as the center of the blood vessel.

(3) The method according to (1), wherein: a distance between two boundaries determined such that a certain width along X-axis of the acquired ultrasound image is extracted, in the extracted width gradient of image energy defined as accumulated brightness in the perpendicular direction to the X-axis, is examined and two maximum point in the gradient are determined as the boundaries and the determined distance is determined as the blood vessel diameter.

(4) The method according to (1), wherein: the robot arm is controlled by two moving degrees of freedom and one rotating degree of freedom.

(5) The method according to (1), wherein: the robot arm is moved and controlled along the X-axis direction in the first step.

(6) The method according to (1), wherein: the robot arm is rotated and controlled around the Z-axis in the second step.

(7) The method according to (1), wherein: the robot arm is moved and controlled along the X-axis direction in the third step.

(8) The method according to (1), wherein the second and the steps respectively further comprise steps of: any one of the ultrasound images acquired during a series of operations is divided by a predetermined width in the X-axis direction into a plurality of segments; a blood vessel diameter in each divided segment is determined; a median value is selected among determined blood vessel diameters; the number of determined blood vessel diameters which fall into a certain range centered by the median value, is calculated; a score value is calculated by dividing the calculated number by the total number of the divided segments; score values calculated from respective series of acquired ultrasound images are compared; and a position having a maximum score value is judged as an optimum position of the ultrasound probe in the second step or the third step.

(9) The method according to (1), wherein: a changing passage after the blood vessel is dilated, is tracked on a real-time basis.

BRIEF DESCRIPTION OF THE DRAWINGS

FIG. 6A shows a procedure for determining the center line of the blood vessel, FIG. 6B shows a procedure for positioning the ultrasound probe in parallel to the center line of the blood vessel and FIG. 6C shows a procedure for positioning the ultrasound probe in parallel to and immediately above the center line of the blood vessel.

DETAILED DESCRIPTION OF PREFERRED EMBODIMENTS

Hereinafter an embodiment according to the present invention is explained in detail by referring to drawings.

Figure 1:
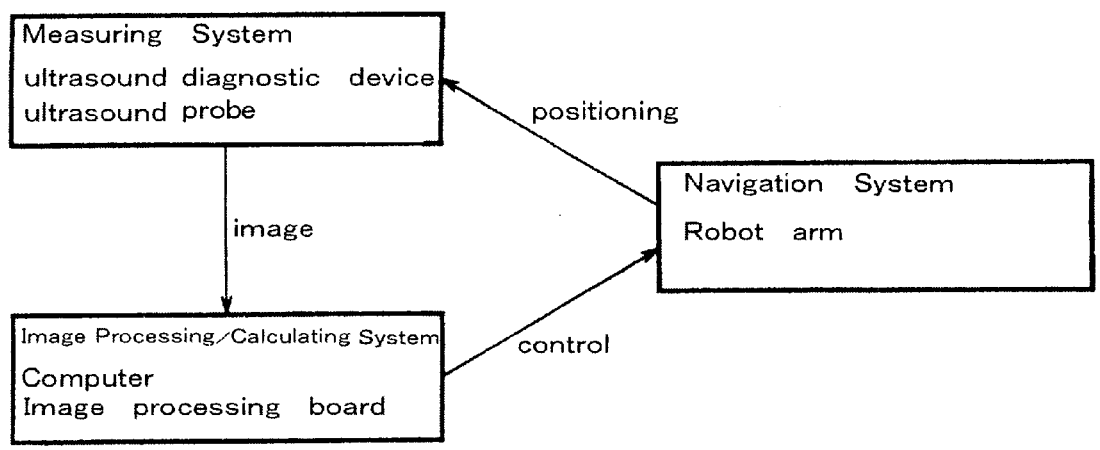
FIG. 1 is a block diagram illustrating a rough arrangement of an automatic examination system for measuring the vascular endothelium function.

FIG. 1 is the block diagram illustrating the rough arrangement of the automatic examination system for measuring the vascular endothelium function, where the measuring system comprises three sub-systems, namely, a measuring system, an image processing and calculating system and a navigating system. The measuring system comprising an ultrasound diagnostic apparatus, an ultrasound probe attached to the ultrasound diagnostic apparatus, acquires ultrasound images. The image processing and calculating system comprising a computer, an image processing board, processes the acquired images by the measuring system, and calculates values to control a motor for driving the robot arm (which will be described hereinafter) based on the processed results. The navigating system comprises the robot arm which holds the ultrasound probe for scanning and for determining positions of the ultrasound probe.

Figure 2:
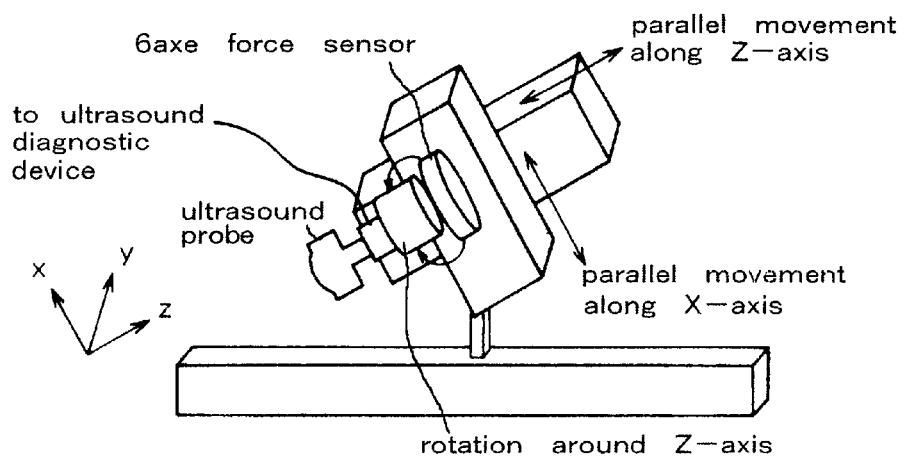
FIG. 2 is a schematic view illustrating functions of a robot arm for holding, moving and rotating an ultrasound probe.

FIG. 2 schematically illustrates an arrangement of the robot arm. The robot arm has two degrees of rotating freedom and two degrees of parallel moving freedom as shown in Table 1 so as to scan and hold the ultrasound probe at optimum positions for acquiring ultrasound images to determine blood vessel diameters, which will be explained below. More specifically, the robot arm equipped with the ultrasound probe is brought to a subject portion to be probed (an arm of the subject) and adjusted its position by controlling within the following four degrees of rotating/moving freedom: a degree of rotating freedom around Y-axis (□45°□□45°) for determining a rough position of the ultrasound probe manually; a degree of moving freedom along Z-axis for laying the center of an ultrasound image on the center of a blood vessel and a degree of moving freedom along X-axis and a degree of rotating freedom around Z-axis for guiding the ultrasound probe to the optimum position to acquire a proper image for determining the blood vessel diameter. Automatically controlled degrees of moving freedom along X-axis and Z-axis are set between □20 mm and □20 mm, since the ultrasound probe is scanned in an image frame having a range of 40 mm by 40 mm. The automatically controlled degree of rotating freedom around Z-axis is set from 70° to 110° in accordance with the other degrees of freedom. Since the size of a pixel of the acquired ultrasound image is enlarged up to 0.05 mm, respective spatial resolutions of moving freedom along X-axis and Z-axis are set 1/20 of the size of the pixel, namely 0.002 mm. A resolution of the rotating freedom around Z-axis is set 0.1° in accordance with the above-mentioned resolutions of moving freedom.

Ranges of strokes of the robot arm shown in Table 1 are one of examples and not limited in these ranges.

TABLE 1

| Specification of Robot Arm | | | |
| --- | --- | --- | --- |
| Controlled | Degree of Freedom | Stroke Range | Resolution |
| Manually | Y-axis Rotation | □45° □□45° | — |
| Automatically | X-axis Movement | □20 mm □□20 mm | □ 0.002 mm |
|  | Z-axis Movement | □20 mm □□20 mm | □ 0.002 mm |
|  | Z-axis Rotation | 70° □110° | □ 0.1° |

Further, a 6-axe force sensor is arranged in the robot arm for sensing a contact pressure of the ultrasound probe against a subject (an arm) so as to keep the contact pressure at a constant level.

Hereinafter a procedure to determine the blood vessel diameters by processing acquired images with the aid of a computer is described.

Figure 3:
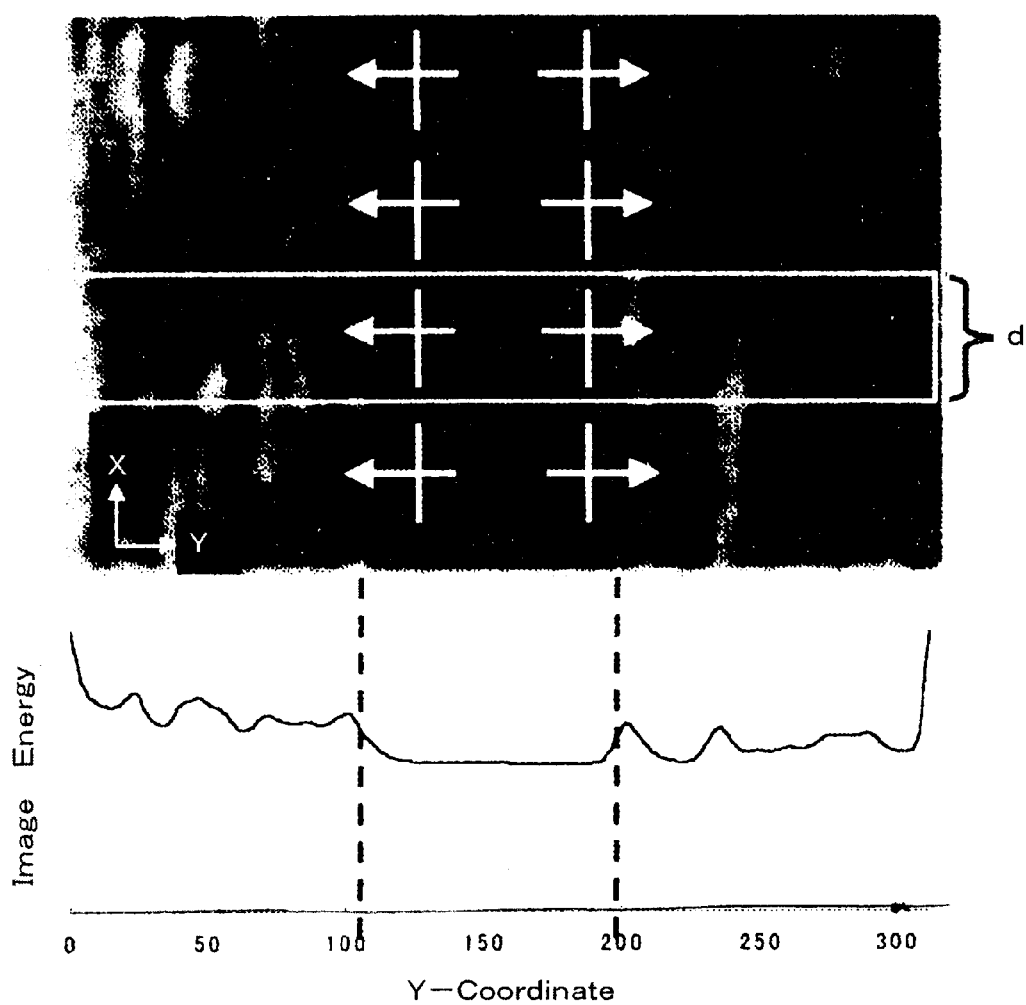
FIG. 3 is an ultrasound image for explaining a determining method of a blood vessel diameter.

A distance between two boundaries formed by a upper/lower vascular wall and a upper/lower vascular lumen is determined from the acquired ultrasound image of the blood vessel in the longitudinal direction as the blood vessel diameter. However, it has been well known that reproducibility of the determined results is poor when extracted boundaries are processed by an ordinarily used edge detecting algorithm, since in the acquired ultrasound image, density of the recognized vascular wall along the longitudinal direction fluctuates irregularly. In the present invention, based on our observed fact that a vascular wall image shows a gradual curve approximating to a straight line, a method for approximating the vascular walls to a plurality of line segments having a predetermined width (line segment method) is employed. In this method, accumulated brightness of pixels existing in a line segment of width "d" along X-axis is defined as image energy and gradient of the image energy is examined in a direction from the center of the vascular lumen to the vascular wall as shown in FIG. 3. A position where the image energy reaches to a threshold value, is defied as a boundary between a vascular lumen and a vascular wall. In FIG. 3, two image energy peaks (which are seen near scale marks 100 and 200 on Y coordinate) are determined as the boundaries. A processed ultrasound image by utilizing the line segment method is depicted in FIG. 4.

Figure 4:
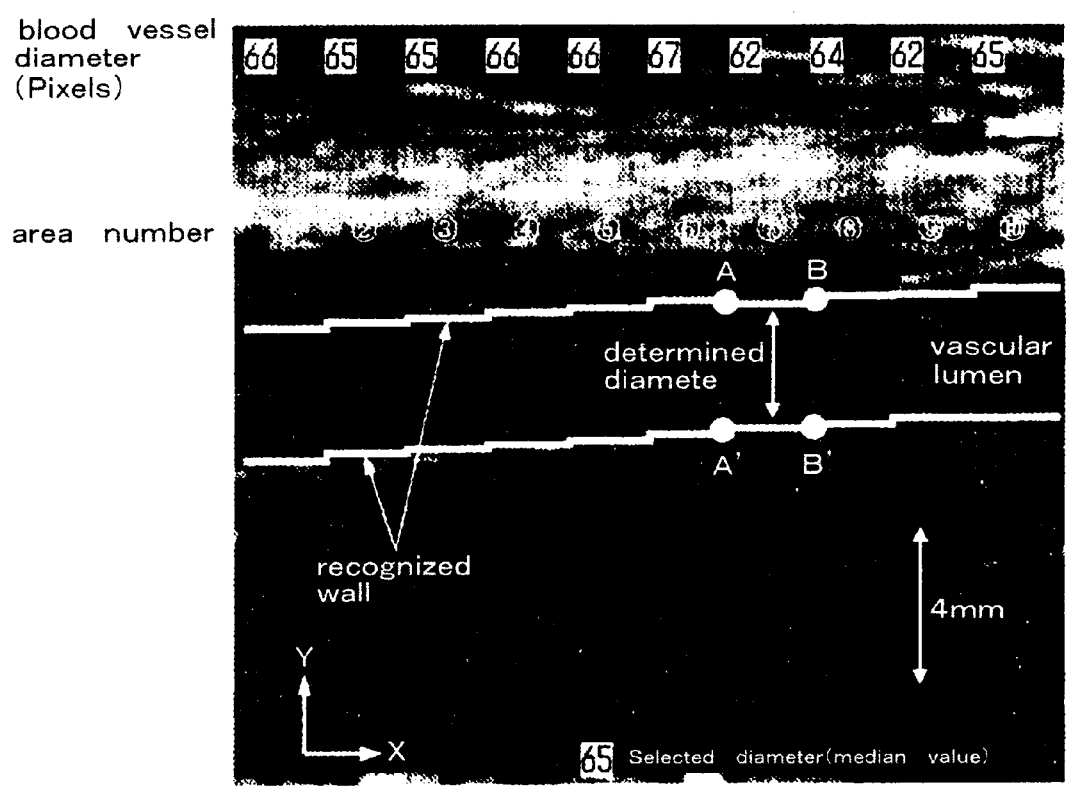
FIG. 4 is an ultrasound image together with determined blood vessel diameters.

Numerals in square (□) at upper portion of FIG. 4 indicate respective vascular diameters expressed in the number of pixels in respective areas 1 to 10 surrounded by circle (○). These numerals (the number of pixels) distribute around 64. Since some numerals (which are apparently considered to be error) apart from other remaining numerals are sometimes recognized, a median numeral is selected as a determined blood vessel diameter so as to avoid influences owing to the above-mentioned numerals considered to be error. The selected median numeral "65" is shown in the square (□) at the lower portion of FIG. 4.

In order to acquire an ultrasound image showing vivid vascular walls proper for determining the blood vessel diameter, the ultrasound probe and the blood vessel should be set at proper positions each other. For that purpose, the ultrasound probe is finally brought to an optimum position starting from rough positioning to fine positioning based on determined blood vessel diameters in the above-mentioned way by processing ultrasound images acquired stepwise by moving/rotating the robot arm within the above-described degrees of moving/rotating freedom. Hereinafter, a positioning procedure for determining the optimum position of the ultrasound probe is described.

Figure 5:
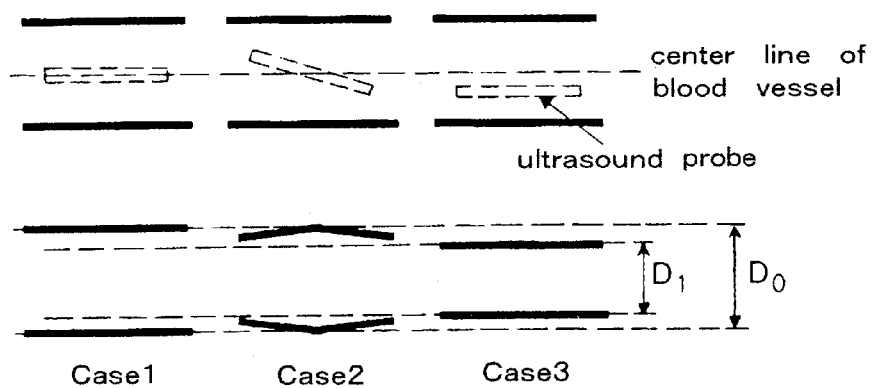
FIG. 5 is a schematic diagram illustrating relations between positions of the ultrasound probe and corresponding acquired images by the ultrasound probe.

Case 1 in FIG. 5 shows a state where the ultrasound probe is properly positioned, namely the probe is positioned parallel to and immediately above the center line of a blood vessel. In this case, an accurate blood vessel diameter $D_0$ is observed as shown in FIG. 5. In case 2 where the ultrasound probe is rotated in a certain angle from the center line of the blood vessel, the accurate value $D_0$ is observed only at a portion which is immediately above the center line. And observed diameters of other portions indicate the smaller than the accurate diameter, the further apart from the center line. In case 3 where the ultrasound probe is positioned parallel to but not immediately above the center line, the observed diameter $D_1$ is smaller than the accurate value $D_0$. From the observed facts mentioned above, only when the ultrasound probe is positioned parallel to and immediately above the center line of the blood vessel, observed diameters indicate maximum value $D_0$, which can be employed as the accurate diameter.

Figure 6A:
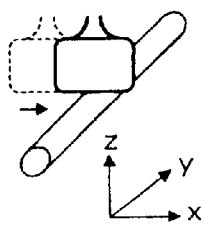
FIGS. 6A to 6C are schematic diagrams illustrating a series of navigating procedures of the ultrasound probe, where
Figure 6B:
Figure 6C:
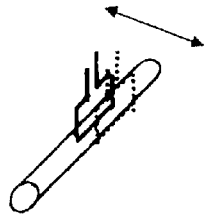

The ultrasound probe is led to an optimum position corresponding to case 1 in FIG. 5 via three steps of automatic navigating procedures, depicted in FIGS. 6A, 6B and 6C.

Before executing the above-mentioned automatic navigating procedures, the ultrasound probe is moved manually to a position where an ultrasound image in the minor axis direction (namely a cross-sectional image perpendicular to the center line) can be acquired. After the ultrasound image is acquired in the above-mentioned way, the ultrasound prove is moved automatically along X-axis such that the center of the blood vessel is brought to the center of the ultrasound image in accordance with the automatic navigation procedure depicted in FIG. 6A. Here the center of gravity of a color Doppler signal area corresponding to a blood flowing area is recognized as the center of the blood vessel.

After the center of the blood vessel is brought to the center of the ultrasound image, the robot arm is rotated angle by angle with a predetermined pitch around Z-axis as shown in FIG. 6B and ultrasound images at respective rotated angles are acquired. The acquired ultrasound images are examined after processed, and a position where a most suitable ultrasound image in the major axis (namely in the parallel direction to the center axis of the blood vessel) for obtaining the blood vessel diameter, is determined.

Whether the ultrasound probe is moved to the optimum position or not is judged by the facts explained in cases 2 and 3 of FIG. 5 that the observed blood vessel diameter indicates smaller value than the accurate diameter when the ultrasound probe deviated from the center of the blood vessel. Based on acquired ultrasound images, a score value for each rotated angle is calculated according to the following equation and a rotated angle having a maximum score value is determined as the optimum position.

Score value $(\%) = n/N \times 100$.

In the above equation, n is the number of blood vessel diameters having pixel number falling into a range of the median value ±1 at a certain rotated angle. In the example shown in FIG. 4, n, namely the number of blood vessel diameters having pixel number 65±1, happened to be 7. N is the total number of blood vessel diameters (line segments) at the same rotated angle and happens to be 10 in the example of FIG. 4. Therefore the score value of this example is determined as 7/10, namely 70%.

Figure 7:
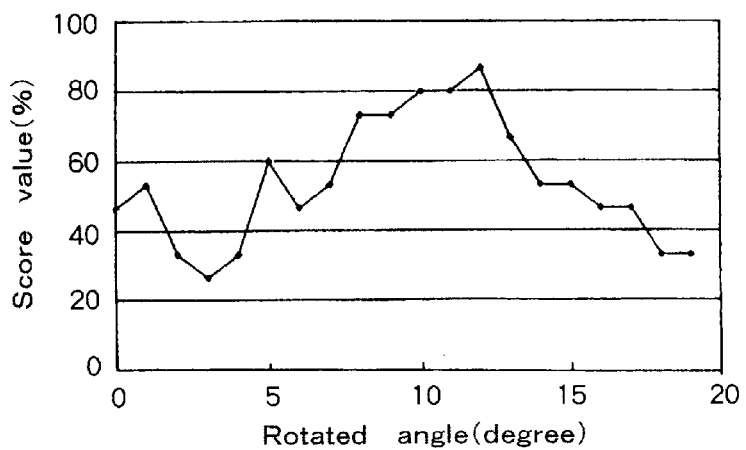
FIG. 7 is a diagram illustrating relations between revolving angles of the ultrasound probe around Z-axis and corresponding score values for positioning depicted in FIG. 6B.

In the above mentioned way score values are calculated and an example of a relation between the score value and the rotated angle is depicted in FIG. 7. In this example a score value at a rotated angle of 12° indicates a maximum value, which is judged as the optimum position of the ultrasound probe.

The ultrasound probe is moved to a parallel position to the center line of the blood vessel by the navigating procedure shown in FIG. 6B, but the ultrasound probe is positioned not always immediately above the center line. Accordingly, the robot arm is moved pitch by pitch with a predetermined distance along X-axis as shown in FIG. 6C and an ultrasound image at each moved angle is acquired. The optimum position of the ultrasound probe is determined in the same way as in the case of procedure depicted in FIG. 6B.

Figure 8:
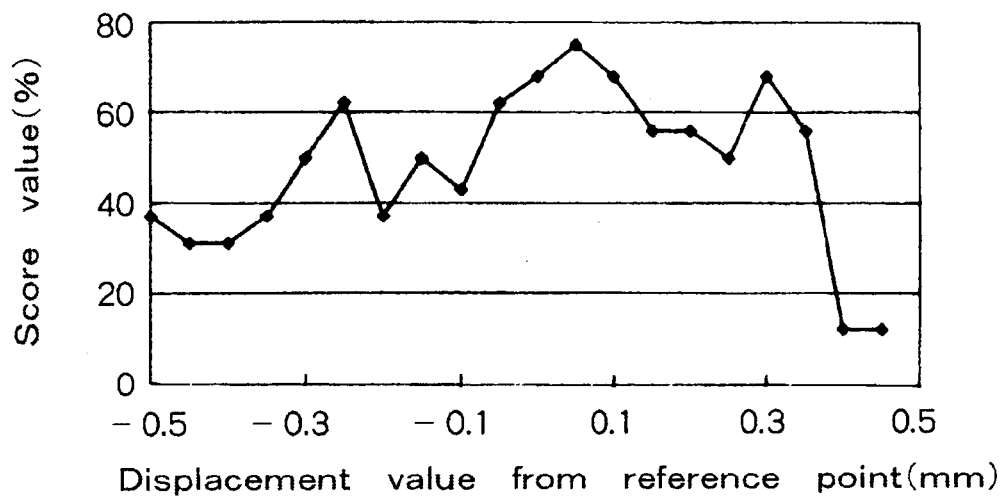
FIG. 8 is a diagram illustrating relations between positions of the ultrasound probe along X-axis and corresponding score values for positioning depicted in FIG. 6C.

FIG. 8 shows an example of a relation between calculated score values and displacements from a reference point, when the ultrasound probe is moved pitch by pitch with a distance of 0.05 mm. In this example a score value at a displacement value of □0.05 indicates a maximum value, which is determined as the optimum point of the ultrasound probe.

The blood vessel diameters and FMD (Flow Mediated Dilation) values are determined by applying the above-described procedures to three subjects (A, B and C; each is healthy person in their twenties).

Determination of Blood Vessel Diameter

In order to prove reproducibility of the above-mentioned determining procedure, 10 determining procedures are carried out in one subject. In each determining procedure, an initial position and an initial angle of the ultrasound probe are varied. Manual determining procedures are also carried out in subject B in order to compare with automatic procedures by the present invention. An average blood vessel diameter (in mm), a score value (in %), a maximum error (in mm) and a standard deviation (in mm) calculated from 10 determining procedures for each subject, and corresponding data by the manual procedure are shown in Table 2.

TABLE 2

Determined Blood Vessel Diameter

|  | Automatic Procedure | | | Manual Procedure |
|---|---|---|---|---|
|  | A | B | C | B |
| Average Diameter (mm) | 3.53 | 3.42 | 3.87 | 3.71 |
| Average Score Value (%) | 77.8 | 55.9 | 44.0 | 38 |
| Maximum Error (mm) | 0.06 | 0.06 | 0.08 | 0.2 |
| Standard Deviation (mm) | 0.04 | 0.03 | 0.04 | 0.14 |

From Table 2, it is evident that a determining precision of the automatic procedure is much improved compared with that of the manual procedure, since maximum errors and standard deviations of the automatic procedure are reduced to a large extent.

Determination of FMD Value

In an examination procedure of the vascular endothelium function, after a blood vessel diameter "d" at rest is determined, a lower portion of the arm is avascularized for 5 minutes by applying 250 mmHg of pressure with a cuff around the arm and released so as to generate a vascular dilating reaction caused by blood flow. During a recovering period of the avascularized arm, a maximum blood vessel diameter $d_{max}$ is determined and the FMD value defined in the following equation is calculated so as to employ as an index for the arterial sclerosis.

$$\text{FMD value } (\%) = (d_{max} - d) \times 100/d$$

Figure 9:
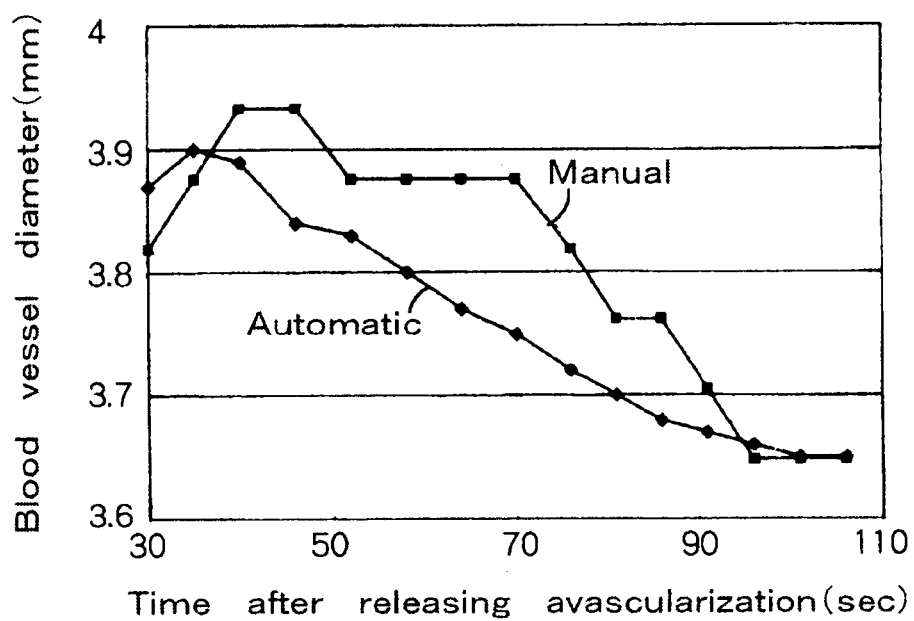
FIG. 9 is a diagram for comparing manual and automatic dilations in respect to blood vessel diameter changes as the passage of time.

In FIG. 9, blood vessel diameters during the recovering period determined by the automatic procedure are plotted in relation the passage of time together with diameters determined by manual procedure. The FMD value is determined in about 2 minute by the automatic procedure on the real time basis in the case shown in FIG. 9. On the other hand, in the manual procedure, it takes about 30 minutes for even a skilled person to determine the FMD value. Consequently, it is obvious that rapid determination of the FMD value is attained by employing the automatic procedure according to the present invention. Determined blood vessel diameters at rest, maximum blood vessel diameters and FMD values of respective subjects A, B and C are shown in Table 3.

TABLE 3

Probed Results of Vascular Endothelium

|  | Subject A | Subject B | Subject C |
|---|---|---|---|
| Diameter at rest (mm) | 3.48 | 3.31 | 3.87 |
| Diameter in | 3.86 | 3.64 | 4.23 |

TABLE 3-continued

Probed Results of Vascular Endothelium

|  | Subject A | Subject B | Subject C |
|---|---|---|---|
| Dilation (mm) |  |  |  |
| FMD value (%) | 11.0 | 10.1 | 9.4 |

Since two FMD values of out of three subjects in TABLE 3 fall into a range from 9.8 to 11.5%, which Hashimoto et al. (the same people referred in the section of "Brief Description of the Related Art") of the medical department of the university of Tokyo, obtained manually from 17 subjects in their twenties. Therefore the automatically determined FMD values mentioned above are considered to be medically proper compared with manually determined values.

As described above, when the examination method of vascular endothelium function by the present invention is employed, the FMD value for employing as the index of the arterial sclerosis can be determined more accurately and rapidly, which were not attained by conventional manual methods. Consequently, the examination method by the present invention can detect the arterial sclerosis (which has been increasing as diets among Japanese people have been varied) much earlier than conventional manual methods.

As explained above, the optimum ultrasound image is obtained and the blood vessel diameter is determined rapidly with good reproducibility by the present invention such that the acquired ultrasound images by the ultrasound probe are analyzed by the computer and then the robot arm which holds the ultrasound probe is controlled by the analyzed results of the ultrasound images. The arterial sclerosis can be detected much earlier when the rapid determining procedure of the blood vessel diameter by the present invention is employed.

What is claimed is:

1. A method of examining a vascular endothelium function by an automatic measurement system comprising:

a measuring system comprising an ultrasound diagnostic device and an ultrasound probe attached to said ultrasound diagnostic device for acquiring an ultrasound image;

an image processing and calculating system comprising a computer and an image processing board for processing the acquired ultrasound image by said measuring system; and a navigation system comprising a robot arm for moving and rotating said ultrasound probe, wherein said method comprises steps of:

a first step wherein an ultrasound image is acquired after said ultrasound probe is moved to a subject portion for probing its vascular endothelium function and said acquired image is processed for calculating and controlling a position of said ultrasound probe so that the center of a blood vessel to be probed is laid on the center of said image;

a second step wherein a series of operations comprising an operation for acquiring ultrasound image, an operation for processing and calculating the acquired ultrasound image and an operation for moving said robot arm based on the calculated result, are repeated starting from the finally acquired ultrasound image at said first step so that said ultrasound probe is moved to in a parallel position to the center line of the blood vessel;

a third step wherein a series of operations comprising an operation for acquiring ultrasound image, an operation for processing and calculating the acquired ultrasound image and an operation for moving said robot arm based on the calculated result, are repeated starting from the finally acquired ultrasound image at said second step so that said ultrasound probe is moved to a position where said ultrasound probe is in parallel to and immediately above the center line of the blood vessel; and a fourth step wherein a blood vessel diameter is determined from the finally acquired ultrasound image at said third step.

2. The method according to claim 1, wherein:

the center of gravity of a color Doppler signal area in the acquired ultrasound image is recognized as the center of the blood vessel.

3. The method according to claim 1, wherein:

a distance between two boundaries determined such that a certain width along X-axis of the acquired ultrasound image is extracted, in the extracted width gradient of image energy defined as accumulated brightness in the perpendicular direction to the X-axis, is examined and two maximum point in said gradient are determined as said boundaries and said determined distance is determined as the blood vessel diameter.

4. The method according to claim 1, wherein:

said robot arm is controlled by two moving degrees of freedom and one rotating degree of freedom.

5. The method according to claim 1, wherein:

said robot arm is moved and controlled along the X-axis direction in said first step.

6. The method according to claim 1, wherein:

said robot arm is rotated and controlled around the Z-axis in said second step.

7. The method according to claim 1, wherein:

said robot arm is moved and controlled along the X-axis direction in said third step.

8. The method according to claim 1, wherein said second and third steps respectively further comprise steps of:

any one of the ultrasound images acquired during a series of operations is divided by a predetermined width in the X-axis direction into a plurality of segments;

a blood vessel diameter in each divided segment is determined;

a median value is selected among determined blood vessel diameters;

the number of determined blood vessel diameters which fall into a certain range centered by said median value, is calculated;

a score value is calculated by dividing said calculated number by the total number of the divided segments;

score values calculated from respective series of acquired ultrasound images are compared; and a position having a maximum score value is judged as an optimum position of said ultrasound probe in said second step or third step.

9. The method according to claim 1, wherein:

a changing passage after the blood vessel is dilated, is tracked on a real-time basis.

* * * * *